United States Patent
Fujiwara et al.

(10) Patent No.: US 10,354,019 B2
(45) Date of Patent: Jul. 16, 2019

(54) RECORDING MEDIUM, DENTAL PROSTHESIS DESIGN APPARATUS, AND DENTAL PROSTHESIS DESIGN METHOD

(71) Applicant: FUJITSU LIMITED, Kawasaki-shi, Kanagawa (JP)

(72) Inventors: Toshihisa Fujiwara, Yokosuka (JP); Toshiaki Mase, Yokohama (JP); Guoping Sun, Kawasaki (JP); Junichi Arai, Nagano (JP)

(73) Assignee: FUJITSU LIMITED, Kawasaki (JP)

( * ) Notice: Subject to any disclaimer, the term of this patent is extended or adjusted under 35 U.S.C. 154(b) by 992 days.

(21) Appl. No.: 14/817,725

(22) Filed: Aug. 4, 2015

(65) Prior Publication Data

US 2015/0335406 A1 Nov. 26, 2015

Related U.S. Application Data

(63) Continuation of application No. PCT/JP2013/056687, filed on Mar. 11, 2013.

(51) Int. Cl.
- *G06F 17/50* (2006.01)
- *A61C 13/00* (2006.01)
- *A61C 5/77* (2017.01)
- *A61C 13/34* (2006.01)

(52) U.S. Cl.
CPC .......... *G06F 17/50* (2013.01); *A61C 5/77* (2017.02); *A61C 13/0004* (2013.01); *A61C 13/34* (2013.01)

(58) Field of Classification Search
CPC ....... G06F 17/20; A61C 5/77; A61C 13/0004; A61C 13/34

USPC .............................................................. 703/6
See application file for complete search history.

(56) References Cited

U.S. PATENT DOCUMENTS

| 2006/0195419 A1 | 8/2006 | Tenma et al. |
| 2008/0108014 A1 | 5/2008 | Holzner et al. |
| 2008/0319448 A1* | 12/2008 | Lavallee ............ G06F 19/3437 606/102 |

(Continued)

FOREIGN PATENT DOCUMENTS

| EP | 1195226 | 4/2002 |
| EP | 1304088 A1 | 4/2003 |

(Continued)

OTHER PUBLICATIONS

Extended European Search Report dated Feb. 17, 2016 for corresponding European Patent Application No. 13878450.9, 6 pages.

(Continued)

*Primary Examiner* — Brian S Cook
(74) *Attorney, Agent, or Firm* — Fujitsu Patent Center

(57) ABSTRACT

A computer-readable recording medium having stored herein a program for causing a computer to execute a dental prosthesis design process includes: searching a database storing data including structures of teeth including natural teeth to search for candidate teeth, which correspond to a part where a prosthesis is to be mounted on, based on information of a shape surrounding the part where the prosthesis is to be mounted on; putting priority levels on the candidate teeth by applying a predetermined rule to a matching degree of the searching; and outputting information of the candidate teeth based on the priority levels.

15 Claims, 12 Drawing Sheets

(56) References Cited

U.S. PATENT DOCUMENTS

| | | | |
|---|---|---|---|
| 2010/0049351 A1* | 2/2010 | Monkmeyer | A61C 5/77 700/98 |
| 2011/0125304 A1 | 5/2011 | Schneider et al. | |
| 2011/0244429 A1 | 10/2011 | Waizenegger et al. | |
| 2012/0322025 A1 | 12/2012 | Ozawa et al. | |

FOREIGN PATENT DOCUMENTS

| | | |
|---|---|---|
| JP | 02-219179 | 8/1990 |
| JP | 5-49651 A | 3/1993 |
| JP | 08-180061 | 7/1996 |
| JP | 09-019443 | 1/1997 |
| JP | 2609320 | 5/1997 |
| JP | 2000-107203 | 4/2000 |
| JP | 2001-001229 | 1/2001 |
| JP | 2005-168518 | 6/2005 |
| JP | 2008-114079 | 5/2008 |
| JP | 2010-503437 A | 2/2010 |
| JP | 4464485 | 5/2010 |
| JP | 2010-269034 | 12/2010 |
| JP | 2011-110420 | 6/2011 |
| JP | 2012-016573 | 1/2012 |
| WO | 2005-052819 | 6/2005 |
| WO | 2011/102118 A1 | 8/2011 |

OTHER PUBLICATIONS

International Search Report and Written Opinion of the International Searching Authority (Form PCT/ISA/210, Form PCT/ISA/237), mailed in connection with PCT/JP2013/056687 and dated Jun. 11, 2013, with partial English translation (8 pages).

Japanese Office Action dated Jan. 17, 2017 for corresponding Japanese Patent Application No. 2015-505110, with Partial English Translation, 5 pages. Please note JP-9-19443, JP-8-180061 and WO-2005/052819 cited herewith, were previously cited in an IDS filed on Aug. 4, 2015.

Japanese Office Action dated Mar. 6, 2018 for corresponding Japanese Patent Application No. 2017-081355, with English Translation, 7 pages. Please note JP-2000-107203-A and JP-2012-16573-A cited herewith, were previously cited in an IDS filed on Aug. 4, 2015.

Chinese Office Action dated Dec. 5, 2016 for corresponding Chinese Patent Application No. 201380074220.2, with English Translation, 12 pages. Please note US-2010049351-A1 cited herewith, was previously cited in an IDS filed on Mar. 9, 2016.

Japanese Office Action dated Jun. 14, 2016 for corresponding Japanese Patent Application No. 2015-505110, with Partial English Translation, 6 pages. Please note JP-2000-107203, JP-9-19443, JP-2012-16573, JP-8-180061 and WO-20051052819 cited herewith, were previously cited in an IDS filed on Aug. 4, 2015.

Chinese Office Action dated Apr. 5, 2016 for corresponding Chinese Patent Application No. 201380074220.2, with English Translation, 16 pages. Please note US2010049351A1 and EP1304088A1 cited herein, were previously cited in an IDS filed on Mar. 9, 2016.

* cited by examiner

FIG.7

| HUMAN ID OR TOOTH ID | POSITION | AXIAL INFORMATION ADDRESS | SHAPE INFORMATION ADDRESS | LAYOUT INFORMATION ADDRESS | SHAPE CHARACTERISTICS | USE HISTORY INFORMATION ADDRESS |
|---|---|---|---|---|---|---|
| M501 | UL4 | 2100 | 3100 | 4100 | A | 5100 |
| M501 | UL5 | 2200 | 3200 | 4200 | B | 5200 |

ENTRY 1 →
ENTRY 2 →

FIG.11A
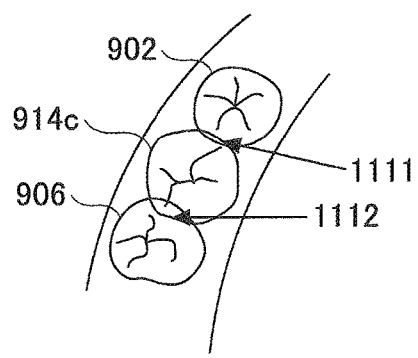
FIG.11B
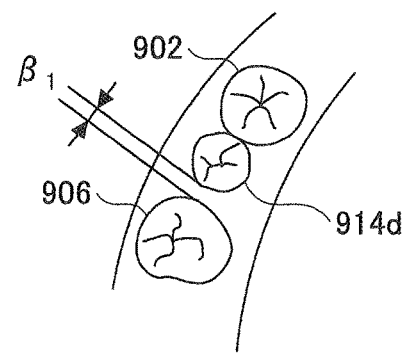
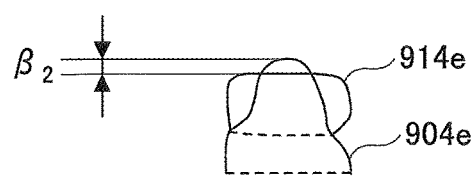
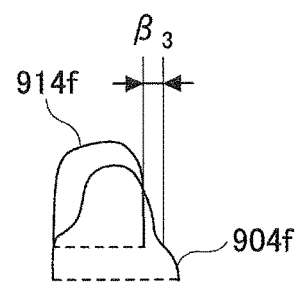
FIG.11C
FIG.11D

FIG.12A
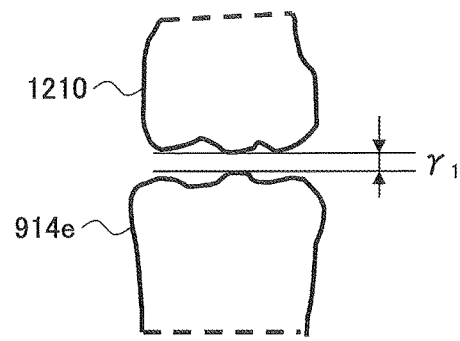
FIG.12B
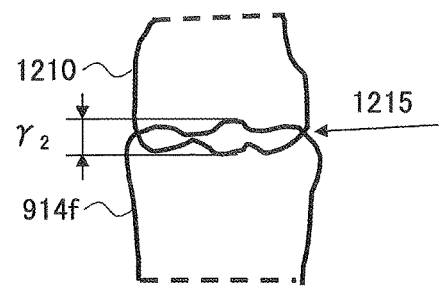
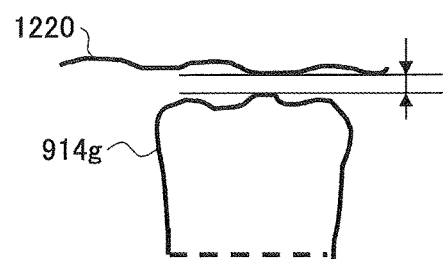
FIG.12C
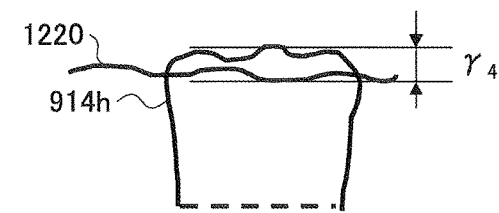
FIG.12D

US 10,354,019 B2

RECORDING MEDIUM, DENTAL PROSTHESIS DESIGN APPARATUS, AND DENTAL PROSTHESIS DESIGN METHOD

CROSS-REFERENCE TO RELATED APPLICATION

This application is a continuation application of International Application PCT/JP2013/056687 filed Mar. 11, 2013 and designating the U.S., the entire contents of which are incorporated herein by reference.

FIELD

The embodiments discussed herein are related to a recording medium, a dental prosthesis design apparatus, and a dental prosthesis design method.

BACKGROUND

In dental treatment, there is a technique used in which a prosthesis such as an inlay or a crown is fabricated by using CAD/CAM. However, the tooth where the prosthesis is to be implemented has already been lost. Due to this, even in the CAD/CAM technique, it is desired to finely adjust the interference or separation with adjacent teeth in the oral cavity. As a result, an operator performs manual operations on a trial-and-error basis very often.

There exists a working method for working a dental prosthesis block into an inlay using a CAD/CAM apparatus. The working method includes dividing a working part to be worked on for an object shape into plural working areas, approximating the objective shapes on the working area basis, roughly working up to an enlarged shape or an offset shape, and finish working on the object shape based on the roughly worked shapes. By doing this, it becomes possible to reduce the influence of the size and the operations of a working jig, and to make a fine replica (see, for example, Japanese Patent No. 4464485).

Further, there exists a technique related to a method for generating a digital model of a dental prosthesis part such as an abutment. The generation method includes a step of evaluating scan data to detect at least a part of a shape of a dental prosthesis model, and a step of evaluating scan data to detect at least the position of a device that protects the dental prosthesis part (see, for example, Japanese Laid-open Patent Publication No. 2008-114079).

Further, there exists a technique providing a combination structure of a fixing part which fixes a tooth shaped part disposed at the position where a tooth is missing by contact while covering one or both of the side surfaces of adjacent teeth or the gingiva, and performs the protection of the tooth-missing area with aesthetic property and the prevention of disturbance after the implanting of the dental implant. When the CAD/CAM method is used, a more accurate prosthesis substitute can be formed by forming the prosthesis substitute based on digital data of the tooth-missing part and the surroundings. Thus, the formed dental prosthesis can suit the tooth-missing area, and the fixing property can be improved (see, for example, Japanese Laid-open Patent Publication No. 2010-269034).

There exists a technique which detects the interference not only between parts but also between various mechanisms located at the periphery of a printed board, between an apparatus and a part, and between the mechanism and the apparatus (see, for example, Japanese Patent No. 2609320).

SUMMARY

According to an aspect of the present application, a computer-readable recording medium stores a program for causing a computer to execute a dental prosthesis design process. The dental prosthesis design process includes searching a database storing data including structures of teeth including natural teeth to search for candidate teeth, which correspond to a part where a prosthesis is to be mounted, based on information of a shape surrounding the part where the prosthesis is to be mounted; putting priority levels on the candidate teeth by applying a predetermined rule to a matching degree of the searching; and outputting information of the candidate teeth based on the priority levels.

The objects and advantages of the embodiments disclosed herein will be realized and attained by means of the elements and combinations particularly pointed out in the claims.

It is to be understood that both the foregoing general description and the following detailed description are exemplary and explanatory and are not restrictive of the invention as claimed.

BRIEF DESCRIPTION OF DRAWINGS

FIG. 7 illustrates an example structure of data stored in the database;

FIGS. 11A through 11D illustrate adjacent teeth and abutment teeth of patients and example detections of interference/separation with the searched-for teeth;

FIGS. 12A through 12D illustrate examples of opposing teeth of a patient and the interference/separation with the searched-for teeth.

DESCRIPTION OF EMBODIMENT

In the following, embodiments of the present invention are described with reference to the accompanying drawings.

Figure 1:
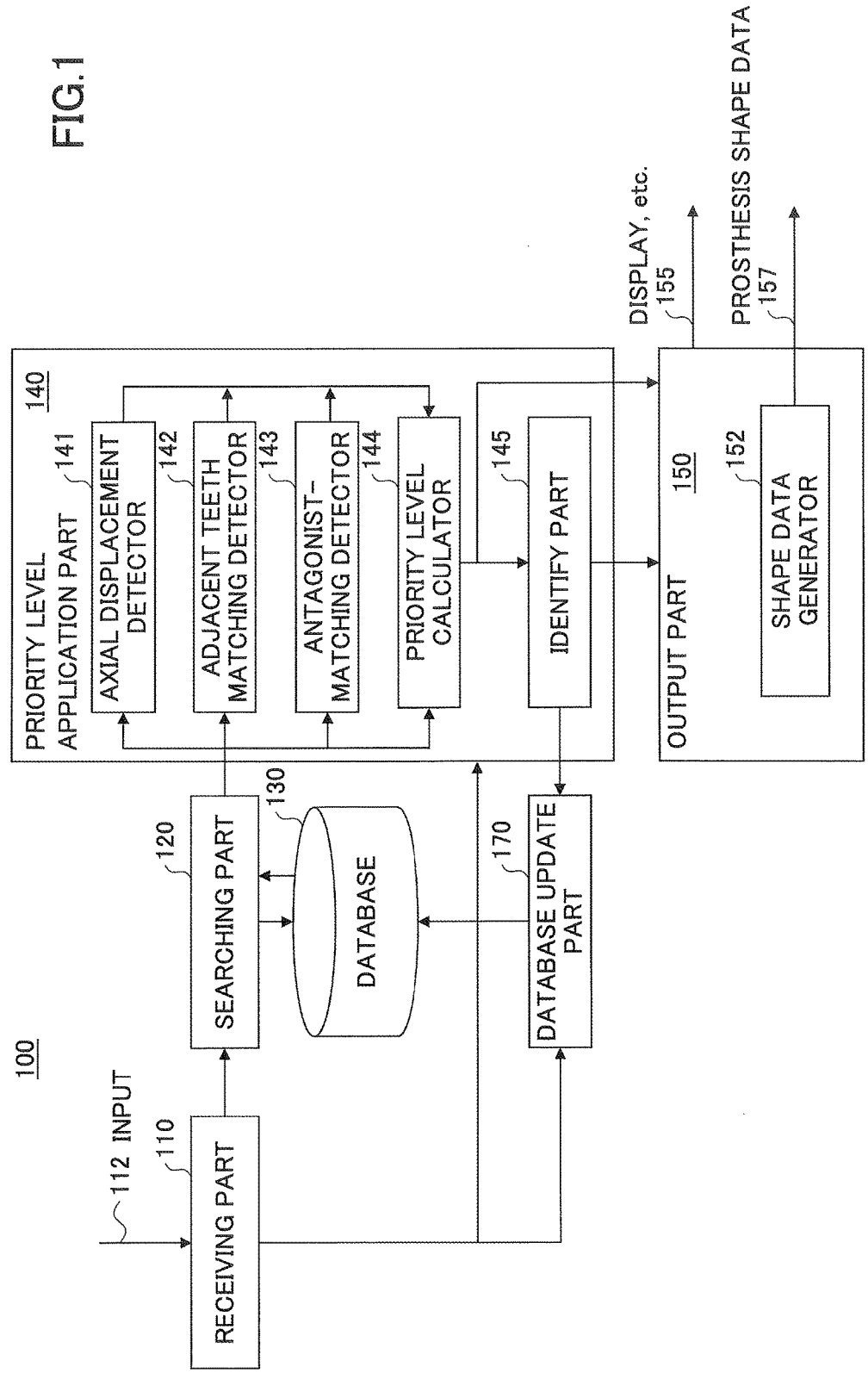
FIG. 1 is a block diagram illustrating an outline of a apparatus according to an embodiment.

FIG. 1 is a block diagram of an outline of a dental prosthesis design apparatus 100. The dental prosthesis design apparatus 100 may include a receiving part 110, a searching part 120, a database 130, a priority level application part 140, an output part 150, and a database update part 170.

The receiving part 110 can receive various inputs 112 from measurement equipment measuring shape information in an oral cavity, etc., by a dental technician, a doctor, or an operator. The receiving part 110 can be connected to various input devices (e.g., a keyboard, a mouse, a touch panel, etc.) or the measurement equipment related to the shape of the oral cavity. As the method of measuring the shapes of the teeth in the oral cavity, for example, a known three-dimensional measurement method of the oral cavity may be used. Further, the result of the three-dimensional measurement of the oral cavity may be provided based on a plurality of polygons. Further, the three-dimensional data based on the polygons may be directly input from another piece of equipment.

The receiving part 110 can transmit the received information to the searching part 120, the database update part 170, the priority level application part 140, etc.

Among the data received by the receiving part 110, as the information to be transmitted to the searching part 120, as described above, the shape information of the oral cavity of a patient may be included. For example, the receiving part 110 can transmit the shape information of the teeth on both sides of the tooth to be treated of the patient (hereinafter referred to as "adjacent teeth") to the searching part 120. However, when there exist only one tooth (as one of the adjacent teeth), the information of the adjacent teeth may have the information of only the one tooth adjacent to the tooth to be treated. Further, in place of or in addition to the information of the adjacent teeth, additional information of the oral cavity may be transmitted to the searching part 120. As the additional information of the oral cavity, there is, for example, the information of the gingiva, etc. The information of the gingiva may be stored in advance, so that the information of the gingiva which is input can be used in searching.

Figure 8A:
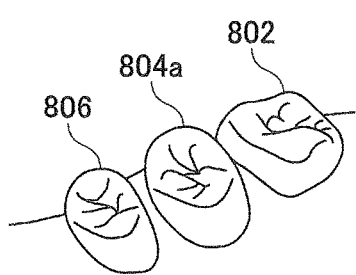
FIGS. 8A and 8B illustrate an example structure of a treated tooth.

FIG. 8A illustrates teeth. As the tooth which has been treated, a tooth 804*a* is illustrated. The specific adjacent teeth relative to the tooth 804*a* are teeth 802 and 804.

Figure 8B:
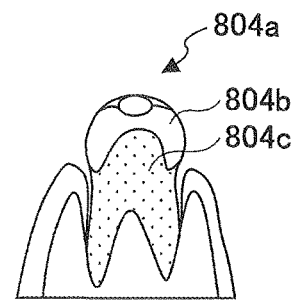

FIG. 8B is a cross-sectional view of the treated tooth 804*a*. For example, the treated tooth 804*a* includes a tooth crown 804*b* and an abutment tooth 804*c*. Note that FIG. 8B is a simplified cross-sectional view.

According to this embodiment, the data which are necessary to fabricate, for example, the tooth crown 804*b* (e.g., CAD/CAM data) can be acquired easily and rapidly while manual operations performed by an operator can be reduced as much as possible.

Further, note that the shape information of the oral cavity of a patient is not limited to the information of the adjacent teeth. That is, the shape information of the oral cavity may be the shape information of the teeth near the tooth to be treated, the information including gingiva and jawbone, or the information of any part of the above-described information.

In addition, the receiving part 110 may receive the information of the abutment tooth 804*c* of FIG. 8B.

Figure 9B:
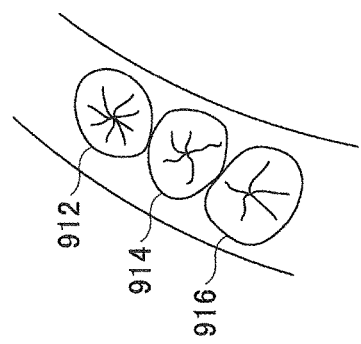
FIGS. 9A through 9C illustrate an example method of searching the database.
Figure 9A:
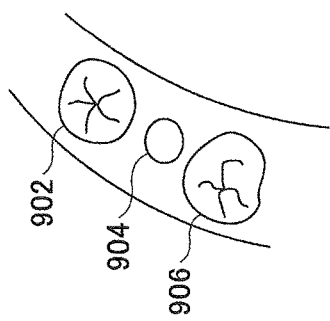

FIG. 9A schematically illustrates the shape information in the oral cavity of a patient. An abutment tooth 904 is illustrated between adjacent teeth 902 and 906. The shape information and the positional information of the abutment tooth 904 may also be acquired as the result of the three-dimensional measurement in the oral cavity. The measurement data may be provided based on polygons, etc.

Referring back to FIG. 1, the searching part 120 searches the database 130 by using, for example, the information of the adjacent teeth, etc., as the shape information in the oral cavity of the patient. As described below, the database 130 stores information of the shape of the teeth including natural teeth, the positional relationship of the teeth in the oral cavity, the inclination of the teeth, etc. Further, the shape of the teeth stored in the database 130 may be a partial shape of the teeth. For example, a partial shape that can be used as a tooth crown on the upper part of the tooth may be stored.

For example, the searching part 120 may use an algorithm of Iterative Closest Point (ICP). In the ICP algorithm, a positional alignment is performed by associating the points in the shape data with each other, performing repeated calculations based on the association, and minimizing the distances therebetween. After the positional alignment is performed, it becomes possible to acquire the data of the search result that, for example, a volume difference between the adjacent teeth and the shape data stored in the database 130 is less than a predetermined threshold value along with the volume difference. Here, the "volume difference" can be used as an index of "matching degree" in the searching, and can be used when the priority level application part 140 determines the priority level of a search result. The volume difference is an example of the information indicating the matching degree of the search result. Therefore, any information other than the volume difference may be used as long as the information can indicate the matching degree of the search result. In place of the volume difference, for example, the maximum value of the displacement (misalignment) of the surface between the adjacent teeth and the shape data stored in the database 130 may be used. Note that, the embodiment is not limited to the volume difference and the maximum value of the displacement of the surface.

FIG. 9B illustrates an example of searched-for data. The teeth 912 and 916 are similar to the input adjacent teeth 902 and 906, respectively. Then the tooth 914 between the teeth 912 and 916 is acquired. The searched-for tooth 914 can be a candidate of the shape of the tooth to be treated of the patient. Note that the number of the search results may be two or more.

The search result acquired here is one example of candidate teeth (candidates of teeth). Note that the searching for the shape date used by the searching part 120 is not limited to the ICP algorithm.

The database 130 can store information including the structures of teeth including natural teeth. FIG. 7 illustrates an example of the data stored in the database 130. Details of FIG. 7 are described below.

Referring back to FIG. 1, the priority level application part 140 may include an axial displacement detector 141, an adjacent teeth matching detector 142, an antagonist-matching detector 143, a priority level calculator 144, and an identify part 145. A rule which is used in a process by the priority level application part 140 is an example of the (claimed) "predetermined rule".

The axial displacement detector 141 is described with reference to FIGS. 10A through 10C.

Figure 10A:
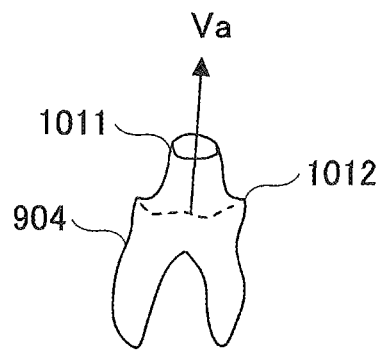
FIGS. 10A through 10C illustrate an example detection of an axial displacement of a searched-for tooth.

FIG. 10A illustrates the abutment tooth 904. FIG. 10B illustrates the tooth 914 which is searched for in the database 130 by the searching part 120. The vector "Va" represents the directional axis of the abutment tooth 904 and the relative position relative to, for example, the teeth on both sides thereof. The vector "Va" may be determined as a vector which passes through the gravity center (geometric center) position of a substantially circular shape formed by a margin line 1012 of the abutment tooth 904 (boundary line with a tooth crown (not shown)) and the gravity center of an uppermost part 1011 of the abutment tooth 904. Note that the determination of the vector is not limited thereto. Further, when the abutment tooth does not exist, the vector which extends vertically from the center of the hole in the gingiva may be used.

The vector "Vb" represents the directional axis of the candidate of the searched-for tooth 914 and the relative position relative to, for example, the teeth on both sides thereof. When the searched for data are the data of the tooth crown, the vector "Vb" may be determined as a vector which passes through the gravity center position of the bottom surface 1022 of the tooth crown and the gravity center of the uppermost part 1021 of the tooth crown. Further, when the searched-for data are the data of whole teeth, the vector "Vb" may be determined as a vector which passes through the gravity center position of a substantially circular shape formed by the line corresponding to the margin line of the abutment tooth and the gravity center of the uppermost part 1021 of the teeth. Note that the determination of the vector is not limited thereto.

Figure 10B:
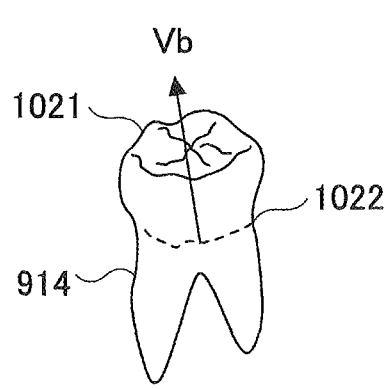
Figure 10C:
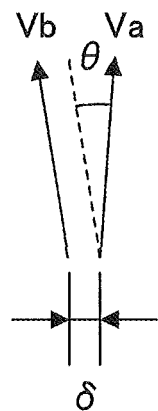

FIG. 10C illustrates the displacement between the vectors "Va" and "Vb". The displacement between the vectors "Va" and "Vb" includes a positional displacement "δ" and a directional displacement "θ". Those two values may be included as a one-dimensional scalar value, that is, an axial displacement amount "G" using the following formula.

$$G = m_1|\delta| + m_2|\theta|$$

Here, $m_1$ and $m_2$ are weighting values, and predetermined values may be used therein. The symbols "δ" and "θ" are values having different dimensions. However, by using the above Formula, it becomes possible to handle as a one-dimensional scalar value of the axial displacement amount "G".

For example, the smaller the value of "G" is, the more the axis of the abutment tooth 904 and the axis of the candidate searched-for tooth 914 approximate each other. Therefore, by designing the tooth crown to cover the abutment tooth 904 based on the candidate searched-for tooth 914 having the approximated axis, it can be expected to reduce a feeling of strangeness perceived by the patient. Note that, however, the handling of the axial displacement is not limited thereto.

The adjacent teeth matching detector 142 of FIG. 1 is described with reference to FIGS. 11A through 11D.

FIGS. 11A through 11D illustrate examples of detection of interference/separation between the adjacent teeth of a patient and the candidate searched-for tooth. In FIG. 11A, on an imaging plane, a candidate tooth 914c is superimposed on the adjacent teeth 902 and 906. In this case, the candidate tooth 914c is too large, so that an interference 1111 occurs relative to the adjacent tooth 902 and an interference 1112 occurs relative to the adjacent tooth 906. In such a case, due to the occurrence of the interference, it is not possible to directly use the shape of the candidate tooth. To quantitatively express the interferences 1111 and 1112, for example, a value of the sum of the depth of the interference 1111 and the depth of the interferences 1112 may be used. Otherwise, a value of the sum of the volumes of the interferences 1111 and 1112 may be used. Note that the embodiment is not limited thereto.

FIG. 11B illustrates a case where a candidate tooth 914d is superimposed on the adjacent teeth 902 and 906. In this case, the candidate tooth 914d is too small, so that a separation (gap) "$\beta_1$" occurs. The degree of the separation may be determined based on the sum of the distances of the separations on both sides thereof.

Although not illustrated, it is assumed that both interference and separation occur at the same time. As such, there may be some interferences and separations between the candidate tooth and the adjacent teeth.

FIG. 11C illustrates a simulation case where a tooth crown 914e as the candidate tooth is placed on the abutment tooth 904e. In this case, the abutment tooth 904e protrudes from the upper part of the tooth crown 914e by a distance "$\beta_2$".

FIG. 11D illustrates a simulation case where a tooth crown 914f as the candidate tooth is placed on the abutment tooth 904f. In this case, the abutment tooth 904f protrudes from a side part of the tooth crown 914f by a distance "$\beta_4$". Further, when there is no existing abutment tooth, it is not necessary to calculate the interference between the candidate tooth and the adjacent teeth.

In this description, in the cases of FIGS. 11A through 11D where the separation may occur, the interference and the separation may be collectively called "interference". It is desired not to employ the candidate tooth where the interference occurs. To that end, it is desired to set in a manner such that the greater the interference amount becomes, the lower the priority level of the candidate tooth when the interference occurs. Otherwise, when the interference occurs, such candidate teeth may be removed from a list of the candidate teeth.

For example, when those plural interferences are expressed in scalar values as an index of adjacent teeth matching, the following Formula may be used.

$$L = ak_1 + bk_2 + ck_3 + dk_4$$

Here, the symbol $k_1$ denotes the sum of the distances of the depths of the interferences between the candidate tooth and the adjacent teeth in FIG. 11A. The symbol $k_2$ denotes the sum of the distances of the separations (gaps) between the candidate tooth and the adjacent teeth in FIG. 11B. The symbol $k_3$ denotes the distances "$\beta_2$" of the protrusion of the abutment tooth 904e to the upper part in FIG. 11C. The symbol $k_4$ denotes the distances "$\beta_3$" of the protrusion of the abutment tooth 904e to the side part in FIG. 11D. Further, the symbols a, b, c, and d are appropriate weighting values. Note that the index of the adjacent teeth matching is not limited thereto.

The antagonist-matching detector 143 of FIG. 1 is described with reference to FIGS. 12A through 12D.

FIGS. 12A through 12D illustrate examples of the detections of the interference/separation between an opposing tooth (antagonist) which is opposite to (faces) the tooth to be treated of a patient and the searched-for tooth. Similar to the case of FIG. 11, the separation may be called "interference".

FIG. 12A illustrates a case where a static separation "$\gamma_1$" occurs between candidate tooth 914e and an opposing tooth 1210. Here, the "static" herein refers to a state when the teeth have been closed naturally without moving the jaw in the left and right direction. Further, the "opposing" herein refers to a state where teeth (upper tooth and lower tooth) opposing each other include a predetermined tooth face with each other. The tooth opposing a (predetermined) tooth is called an "opposing tooth (antagonist)". Note that that the opposing tooth is not always one. That is, there may be case where there are two or more opposing teeth.

FIG. 12B illustrates a case where a static interference 1215 occurs between candidate tooth 914f and the opposing tooth 1210. The interference amount may be represented by the distance "$\gamma_2$" which is the maximum depth of the interference part between the teeth. Alternatively, the interference amount may be represented by the volume where the teeth are overlapped with each other due to the interference.

FIG. 12C illustrates a case where a dynamic separation "$\gamma_3$" occurs between an opposing tooth 914g and a trace of an opposing tooth 1220. Here, the term "trace of an opposing tooth" refers to a trace drawn by the opposing tooth when the jaw is moved in the left and right direction while the teeth have been closed. Further, the "dynamic" herein refers to a state when the jaw is moved in the left and right direction. The trace of an opposing tooth has a three-dimensional shape. In this regard, note that FIG. 12C is a side view drawn in a two-dimensional manner. The trace of an opposing tooth is acquired by having the patient chew a gum-like material, and move the jaw in the left and right direction, so that the trade information can be acquired as the shape of the gum-like material. The acquired shape is measured in three dimensions, so that the acquired shape can be used as the data of the trace of an opposing tooth.

FIG. 12D illustrates a case where a dynamic interference "$\gamma_4$" occurs between an opposing tooth 914h and the trace of an opposing tooth 1220.

For example, those interferences are expressed in a scalar value J as an index of the antagonist-matching by the following Formula.

$$J = n_1\gamma_1 + n_2\gamma_2 + n_3\gamma_3 + n_4\gamma_4$$

Here, the symbol $\gamma_1$ refers to the distance of the separation of FIG. 12A. The symbol $\gamma_2$ refers to the depth of the interference of FIG. 12B. The symbol $\gamma_3$ refers to the separation distance from the trace of the opposing tooth of FIG. 12C. The symbol $\gamma_4$ refers to the distance of the interference depth with the trace of the opposing tooth of FIG. 12D. Further, the separation and the interference do not occur concurrently. When there is a value in one of $\gamma_1$ and $\gamma_2$, the value of the other of $\gamma_1$ and $\gamma_2$ is zero. Similarly, when there is a value in one of $\gamma_3$ and $\gamma_4$, the value of the other of $\gamma_3$ and $\gamma_4$ is zero. Further, the symbols $n_1$, $n_2$, $n_3$, and $n_4$ denote appropriate weighting values. Note that the index of the antagonist-matching is not limited thereto.

Referring back to FIG. 1, the priority level calculator 144 is described. The priority level calculator 144 may calculate priority levels in association with the candidate teeth based on the matching degree acquired by the searching part 120, the axial displacement amount "G" acquired by the axial displacement detector 141, the index "L" of the adjacent teeth matching acquired by the adjacent teeth matching detector 142, and the index "J" of the antagonist-matching acquired by the antagonist-matching detector 143. When the priority level of a tooth candidate t1 is given as $P_{t1}$, by using the matching degree "M" (the greater M becomes, the higher the matching degree becomes), the priority level $P_{t1}$ can be calculated based on the following Formula.

$$P_{t1} = M - (G + L + J)$$

In this case, the greater the value of $P_{t1}$ becomes, the higher the priority level becomes. Further, predetermined weighting values may be multiplied by the respective parameters in the above Formula. Note that the Formula is an example only, and the embodiment is not limited thereto.

Further, the priority level calculator 144 may further acquire incidental information whether the tooth (candidate tooth) is a tooth of the patient, whether the tooth is a tooth that has ever been selected by the user, and whether the tooth has shape characteristics that the user or the patient likes, from the database 130. Further, based on the incidental information, the priority level calculator 144 may correct the priority level $P_{t1}$ by adding a predetermined bias value to the priority level $P_{t1}$.

Further, the priority level calculator 144 may correct the priority level $P_{t1}$ based on the information whether the candidate tooth is a tooth that the patient had before. Otherwise, when the tooth is a tooth of the patient, the priority level calculator 144 send a report of the information to the identify part 145 which is described below to be identified as the candidate tooth having the highest priority level.

In FIG. 1, the identify part 145 receives the information of the candidate teeth on which the respective priority levels are applied from the priority level calculator 144 and, for example, may identify a tooth having the highest priority level. Otherwise, the identify part 145 may cause the output part 150, which is described below, to display a list of candidate teeth having higher priority levels from among the candidate teeth, so as to prompt the user to select the candidate tooth. Further, the identify part 145 may receive the information which identifies the candidate tooth selected by the user. Otherwise, as described above, when the candidate teeth include a tooth of the patient, the identify part 145 may automatically select and identify the tooth.

The identify part 145 may transmit the information of the identified candidate tooth to the output part 150 and the database update part 170.

The database update part 170 may update the database 130 by, for example, incrementing the number of selection times of the candidate tooth based on the information of the identified candidate tooth, the information of the operator, etc.

Further, the database update part 170 may store the information in the database 130, which is related to the shape in the oral cavity of the patient and is received by the receiving part 110. In this case, the database update part 170 may acquire the information related to a part of healthy teeth as the instruction of the operator from among the shape data of the oral cavity of the patient, and store the data to which the information to recognize the healthy teeth part is added or only the healthy teeth part in the database 130. By doing this, it becomes possible to enhance the content of the database 130.

Further, in the database 130, by any of external programs or by input of operator's instructions, any data of the teeth structure including natural teeth are registered on an as needed basis. As described, it is desired to store data as much as possible to enhance the content of the database on an as needed basis so that the searching part 120 can acquire a result having higher matching degree.

The output part 150 may transmit data 155 to a display device (not shown) to display the data 155. Further, the output part 150 may include a shape data generator 152.

The shape data generator 152 may generate the shape data of the prosthesis (tooth crown) to be placed on the abutment tooth based on the information of the identified candidate tooth, the information of the abutment tooth, etc. The shape data generator 152 may transmit prosthesis shape data 157 to a tooth crown fabricator (not shown) of the CAD/CAM apparatus.

As described above, the dental prosthesis design apparatus in this embodiment can drastically simplify the generation of the shape data of the prosthesis such as a tooth crown by effectively using the information of the database including the information of natural teeth.

Operations

Figure 2:
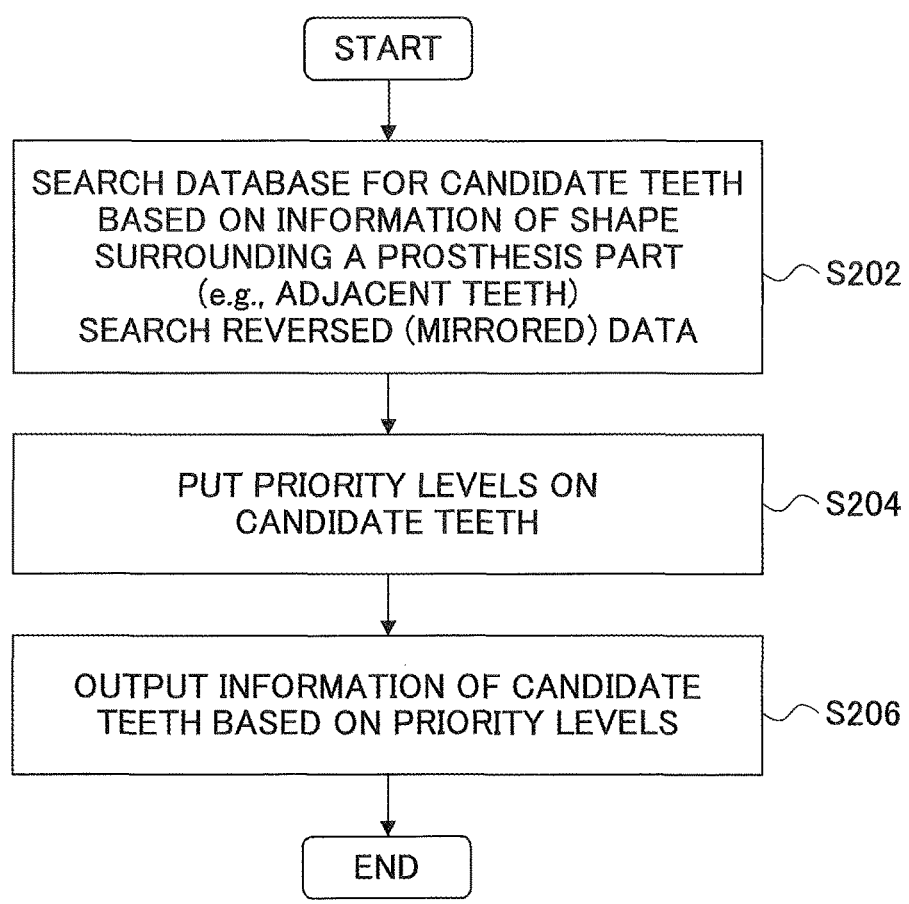
FIG. 2 is a flowchart of an outline of operations according to an embodiment.

In the following, operations according to an embodiment are described with reference to the accompanying drawings. FIG. 2 is a flowchart of an outline of the operations according to one embodiment.

In step S202, the searching part 120 searches for a candidate tooth in the database 130 by using the information of the surrounding shape (e.g., adjacent teeth, etc.) of the tooth on which a prosthesis is to be mounted.

Human teeth are substantially symmetrical between left and right. Due to this, it is also possible to search for mirrored data which are generated by horizontally reversing (in the left and right direction) the data stored in the database 130.

Figure 9C:
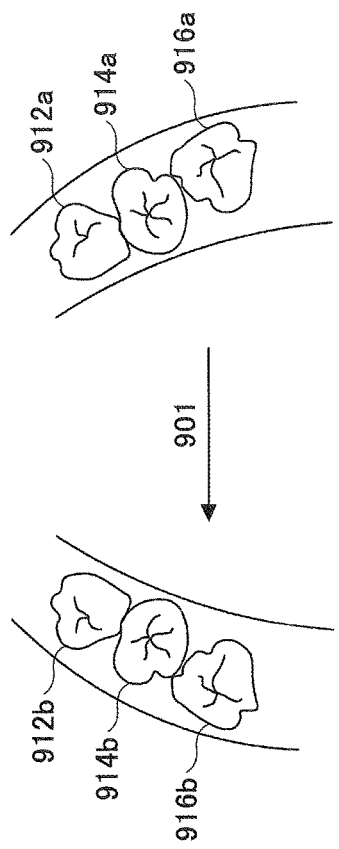

FIG. 9C illustrates the mirroring. For example, when the database 130 stores the information of the teeth 912a, 914a, and 916a on the right side of FIG. 9C, those data can be mirrored (901), so that it becomes possible to search for the mirrored information of the teeth 912b, 914b, and 916b.

Then, as a result, the mirrored candidate of the tooth 914b can be used.

In step S204, the priority level application part 140 puts priority levels on candidate teeth.

In step S206, the output part 150 may output the information related to the candidate teeth based on the priority levels.

Figure 3:
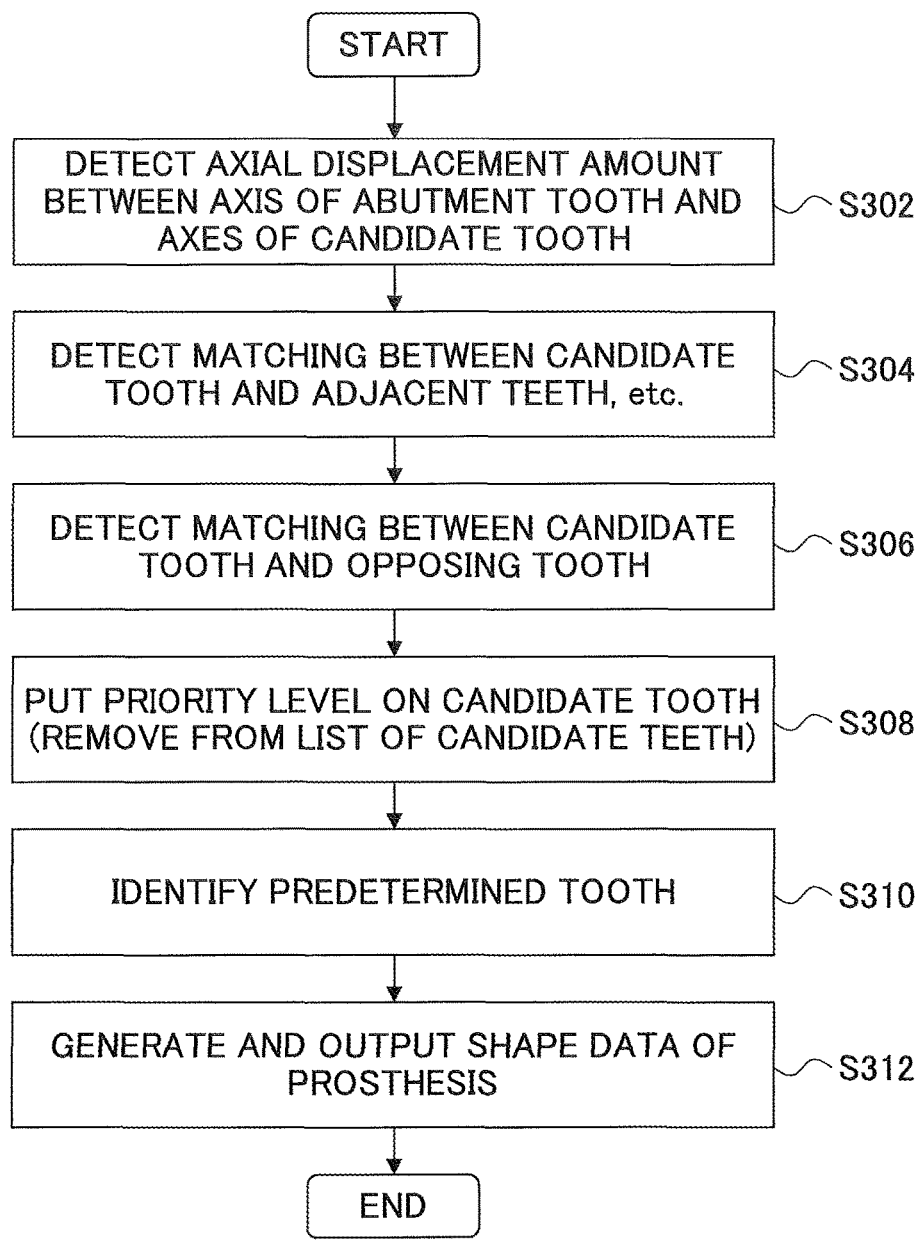
FIG. 3 is a flowchart illustrating an example operation to set a priority level on searched-for tooth candidates.

FIG. 3 is a flowchart of an example operation of putting a priority level on the searched-for tooth.

Further, a priority level is put on the searched for candidate tooth (or tooth crown) based on the matching degree on the searching. The following steps are performed to acquire data to be used so that the priority level is further corrected.

In step S302, the axial displacement detector 141 may detect the axial displacement amount between the axis of the abutment tooth and the axis of the candidate tooth.

In step S304, the adjacent teeth matching detector 142 may detect the matching between the candidate tooth and the adjacent teeth, etc.

In step S306, the antagonist-matching detector 143 may detect the antagonist-matching with the candidate tooth.

In step S308, the priority level calculator 144 may put a priority level on a candidate tooth. Further, the priority level calculator 144 may remove a candidate tooth having a lower priority level.

In step S310, the identify part 145 may identify one tooth from among the candidate teeth having priority levels.

In step S312, the shape data generator 152 of the output part 150 may generate and output the shape data of the prosthesis.

Figure 4:
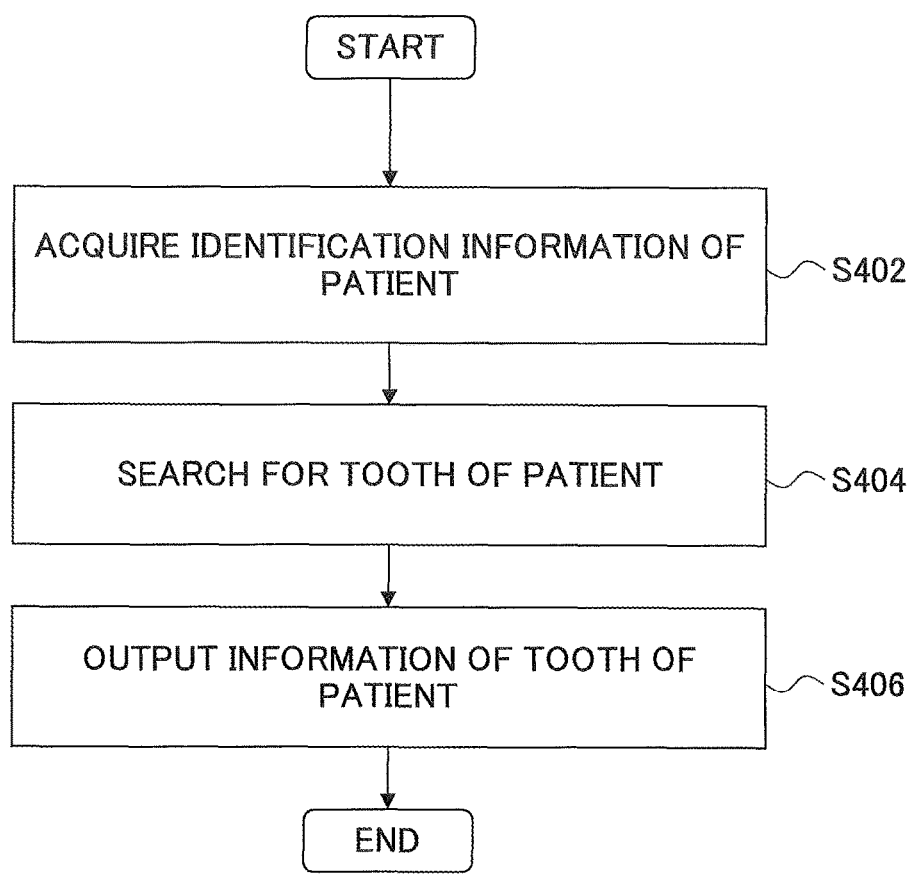
FIG. 4 is a flowchart illustrating another example operation to set the priority level on the searched-for tooth candidates.

FIG. 4 is a flowchart of another example operation of putting a priority level on a searched-for candidate tooth. There may be case where the database 130 stores data which are related to a past tooth of the patient. In this case, it be possible to reproduce the shape of a currently lost tooth so as to have the shape of the past tooth based on the information of the past tooth of the patient.

In step S402, the receiving part 110 receives identification information of the patient.

In step S404, the searching part 120 searches for the tooth of the patient.

In step S406, the identify part 145 outputs the information of the searched-for tooth of the patient to the output part 150.

Figure 5:
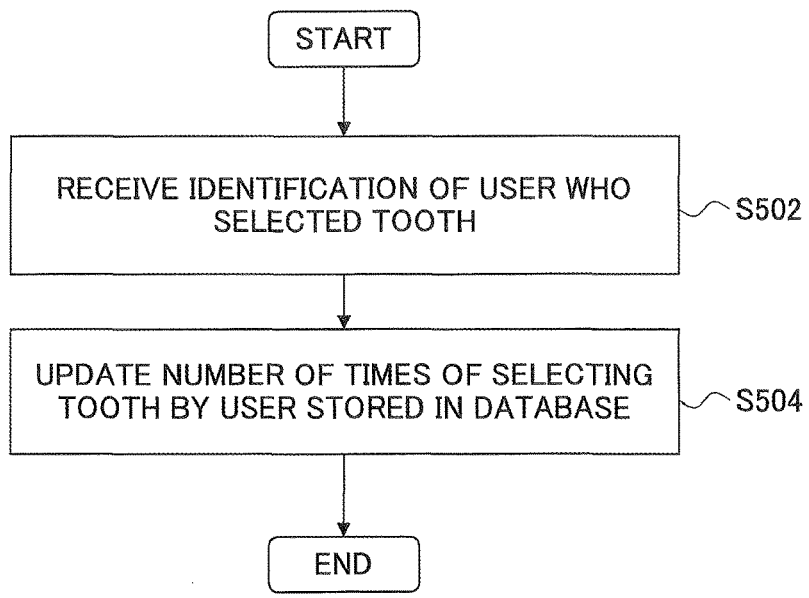
FIG. 5 is a flowchart illustrating an example update of a database.

FIG. 5 is a flowchart of an example update of the database 130.

In step S502, the receiving part 110 receives the identification information of the user who selected the tooth.

In step S504, the database update part 170 updates the number of times of selecting the tooth by the user stored in the database 130.

Figure 6:
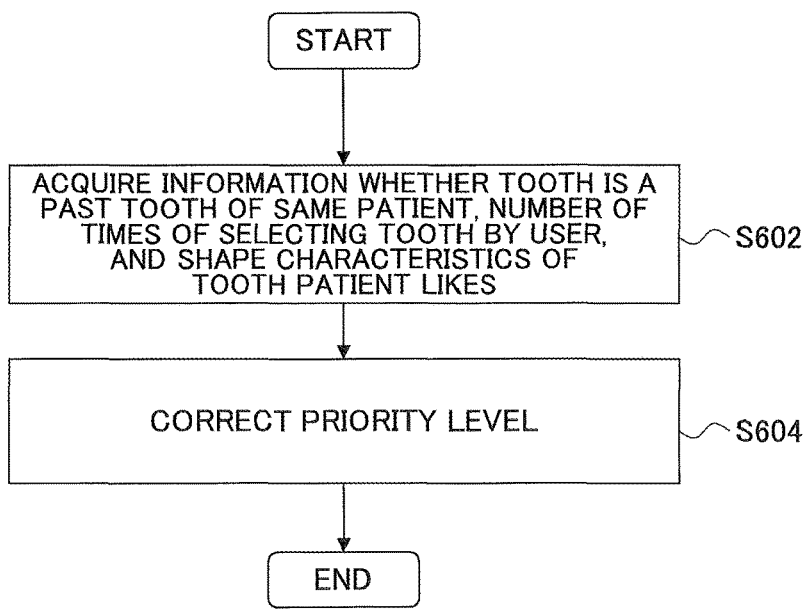
FIG. 6 is a flowchart illustrating an example correction of a priority order.

FIG. 6 is a flowchart of an example correction of a priority order.

In step S602, the priority level calculator 144 acquires the information whether the tooth is a past tooth of the patient, the number of times of selecting the tooth by the user in the past, the information of the user, and the shape characteristics of the tooth that a group of the user or the patient likes from the database 130 via the searching part 120. Further, the number of times of selecting the tooth by the user in the past may not be counted on a user basis, and may be counted regardless of the user and use.

In step S604, the priority level calculator 144 corrects the priority order based on the information described above.

FIG. 7 illustrates example data stored in the database 130. For explanatory purposes, the data are illustrated in a table. Note that, however, a storage format of the data is not limited thereto.

A column 702 may store an ID of the owner of a natural tooth. When the ID of the owner is unknown, an ID of a unique tooth may be stored. For example of Entry 1, "M501" is stored as a human ID.

A column 704 may store, for example, a relational position of a tooth. In Entry 1, data "UL4" are stored. Here, the letter "U" denotes an upper tooth, the letter "L" denotes the left side, and the figure "4" is a tooth row number. By this information, the relational position of the tooth can be identified.

A column 706 stores an axis information address. In Entry 1, a memory address "2100" is stored. In the memory address "2100", for example, the vector "Vb" of the tooth in FIG. 10B may be stored.

A column 708 stores a shape information address. As the shape information, for example, a three-dimensional model of a tooth may be stored. In the address "3100" of Entry 1, as the three-dimensional model, for example, the information using polygons may be used.

A column 710 may store a layout information address. In address "4100" of Entry 1, for example, the information of the relational position in the tooth row may be stored. Here, the layout information may be included in the shape data of the whole oral cavity. Therefore, it is not necessary to have the layout information on a tooth basis.

Note that the embodiment is not limited to the points described above.

A column 712 may store shape characteristics. For example, a round tooth, a pointed tooth, etc., may be stored as the shape characteristics. In Entry 1, data "A" are stored. Here, the "A" may be defined as a pointed tooth. The priority level calculator 144 may conduct matching between the shape characteristic and the characteristics that the user likes, and use the result of the matching to change the priority level of the candidate tooth. Further, association data between a user and the shape characteristics that the user likes may be stored in the database 130 or another memory. Note that such data may not be essential.

A column 714 stores a use history information address. In Entry 1, an address "5100" is stored. In address "5100", for example, an ID of the user who used the data or the number of times of selecting the tooth (not shown) may be stored. The priority level calculator 144 can put a priority order on the candidate teeth which differs depending on a user by using the use history information. By using this, it becomes possible to put a priority order based on the user's preference. Otherwise, the priority order may be corrected not on a user basis but based on a thought that the more the number of times that users select a tooth, the higher the priority level of the tooth becomes.

Note that the information of FIG. 7 is an example only and an information item may be included which is not always desired to be stored in the database 130. Further, as a storage format of the data, any other storage format may be employed.

FIGS. 9A through 9C illustrate example methods of searching the database 130. FIG. 9A illustrates a status of the teeth of a patient, in which there exists the abutment tooth 904 between the adjacent teeth 902 and 906.

FIG. 9B illustrates an example result of searching the database 130, in which there are adjacent teeth 912 and 916 corresponding to the adjacent teeth 902 and 906. To search for a similar shape, for example the ICP described above may be used.

FIG. 9C illustrates that the searching may also be performed on the data of the teeth 912*b*, 914*b*, and 916*b* (left side) which are generated by mirroring (901) the teeth 912*a*, 914*a*, and 916*a* (right side) stored in the database 130.

FIGS. 10A through 10C illustrate an example of detecting the axial displacement of the searched-for tooth, in which the axial direction vector "Va" is of the abutment tooth 904 and the axial direction vector "Vb" is of the candidate tooth 914. As illustrated in FIG. 10C, based on the axial direction vectors "Va" and "Vb", the axial displacement detector 141 calculates the positional displacement "δ" and a directional displacement "θ" between the axes. Based on those calculated data, the axial displacement detector 141 can calculate the axial displacement amount.

FIGS. 11A through 11D illustrate examples of detection of interference/separation between the adjacent teeth and the abutment tooth of a patient and the candidate of the searched-for tooth. As described above, in FIG. 11A, the interference 1111 and interferences 1112 are generated. In FIG. 11B, the separation (gap) "$\beta_1$" is generated. In FIG. 11C, the interference "$\beta_2$" is generated between the abutment tooth 904*e* and the tooth crown 914*e*. In FIG. 11D, the interference "$\beta_3$" is generated between the abutment tooth 904*f* and the tooth crown 914*f*.

Based on the information, the adjacent teeth matching detector 142 can detect the matching between the candidate tooth and the adjacent teeth, etc.

FIGS. 12A through 12D illustrate examples of the detections of the interference/separation between an opposing tooth (antagonist) which is opposite to (faces) the tooth to be treated of a patient and the searched-for tooth. Between the candidate tooth and the opposing tooth, the static separation "$\gamma_1$" or the static interference "$\gamma_2$" occurs. Further, between the candidate tooth and the trace of an opposing tooth, the dynamic separation "$\gamma_3$" or the dynamic interference "$\gamma_4$" occurs. When such a separation or an interference occurs, it is often the case that the candidate tooth is not an appropriate candidate.

As described above, the antagonist-matching detector 143 can detect the matching between the candidate tooth and the opposing tooth.

Figure 13:
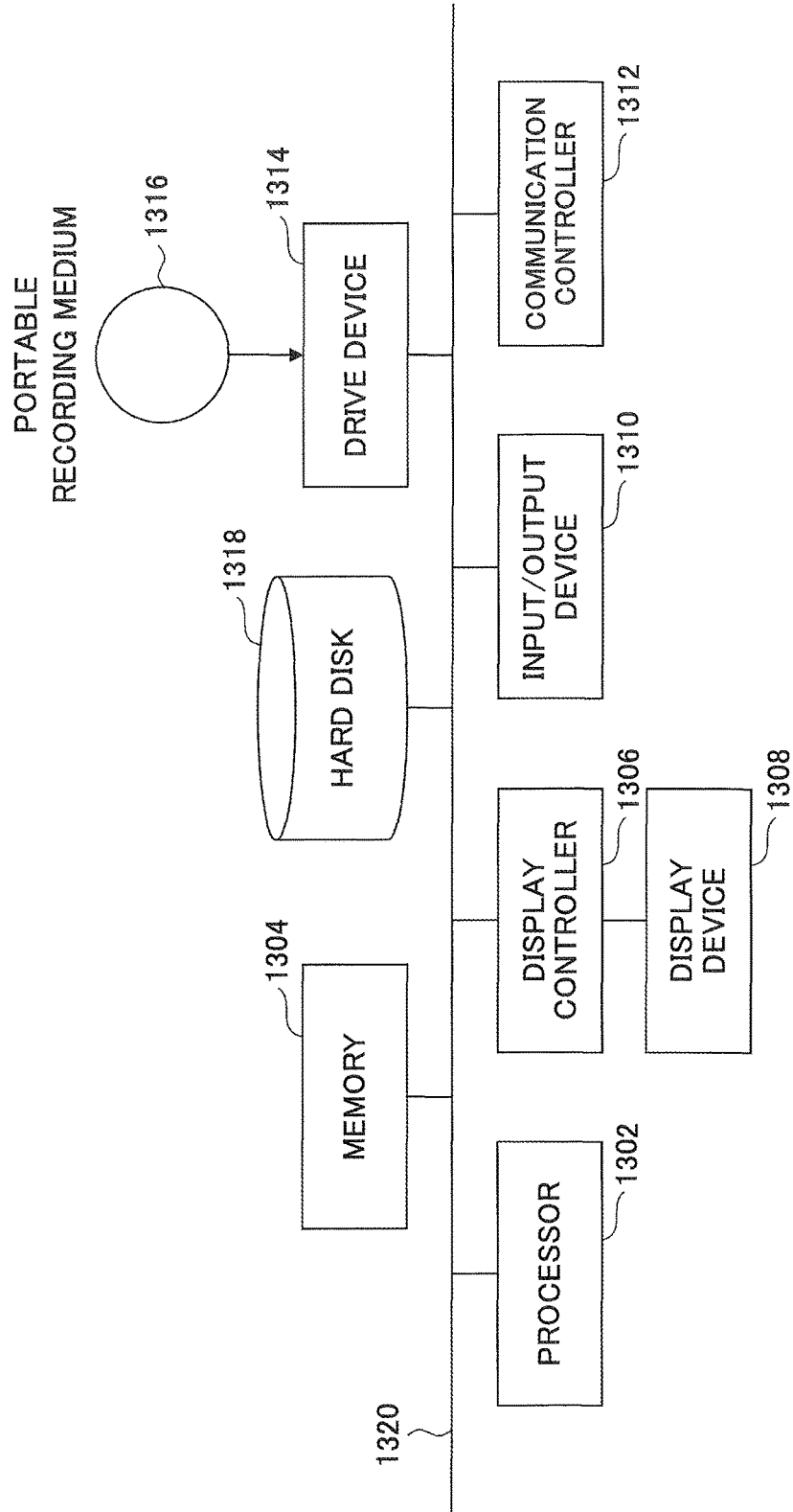
FIG. 13 illustrates a hardware configuration according to an embodiment.

FIG. 13 illustrates an example hardware configuration according to an embodiment. The hardware may include a processor 1302, a memory 1304, a display controller 1306, a display device 1308, an input/output device 1310, a communication controller 1312, a drive device 1314, and a hard disk 1318. Those devices are connected to each other via a bus 1320. Further, the drive device 1314 reads and writes data from and to a portable recording medium 1316. Further, the communication controller 1312 can be connected to a network (not shown). In the hard disk 1318 and/or the memory 1304, a source program and the management information to manage the version of the source may be stored.

A part or all a program according to an embodiment may be stored in the memory 1304, a hard disk 1318, etc., and may be operated by the processor 1302.

A part or all of the embodiments may be implemented by a program, which may be stored in the portable recording medium 1316. Here, the portable recording medium 1316 refers to one or more non-transitory recording media having a structure. As the portable recording medium 1316, there are, for example, a magnetic recording medium, an optical disk, a magneto-optical recording medium, and a non-volatile memory. The magnetic recording medium includes a Hard Disk Drive (HDD), a Flexible Disk (FD), Magnetic Tape (MT), etc. The optical disk includes a Digital Versatile Disc (DVD), a DVD-Random Access Memory (DVD-RAM), a Compact Disc-Read Only Memory (CD-ROM), a CD-Recordable/ReWritable (CD-R/RW), etc. The magneto-optical recording medium includes a Magneto-Optical (MO) Disk, etc. A part or all of an embodiment can be performed by reading a program stored in the portable recording medium and executing the program by the processor.

As described above, details of the embodiments of the present invention are described. Note that, however, the above embodiments are described to understand the present invention, and do not limit the scope of the present invention. Further, note that the embodiments described above are not exclusive of each other. Therefore, note that, unless contradiction occurs, the description is intended to combine elements in different embodiments. Further, note that the order of the processes may be changed, a process may be removed, or some processes may be executed simultaneously unless contraction occurs in the invention related to claimed method and program. Further, needless to say that those embodiments are included in the technical scope of the invention described in claims.

Further, needless to say that not only a case where the functions of the above embodiments are realized by executing the program codes read by the computer but also a case where based on the instructions of the program codes, programs such as an OS, a Virtual Machine Monitor (VMM), firmware, a BIOS, etc., which are operating on the computer, perform a part or all the actual processes, so that the functions of the embodiments realized by the processes are included in the present invention.

Further, each of the configuration elements in the embodiments of the present invention may be realized by a plurality of hardware units which are separated from each other. Further, each of the configuration elements in the embodiments of the present invention may be realized by the operations executed on one or more servers. Further, the number of the CPUs executing a program according to the present invention may be two or more, and each CPU may include a plurality of cores.

All examples and conditional language recited herein are intended for pedagogical purposes to aid the reader in understanding the invention and the concepts contributed by the inventor(s) to furthering the art, and are to be construed as being without limitation to such specifically recited examples and conditions, nor does the organization of such examples in the specification relate to a showing of superiority or inferiority of the invention. Although the embodiments of the present invention have been described in detail, it is to be understood that various changes, substitutions, and alterations could be made hereto without departing from the spirit and scope of the invention.

What is claimed is:

1. A non-transitory computer-readable recording medium having stored therein a program for causing a computer to execute a computer-implemented process to obtain data for producing a dental prosthesis, the process comprising:

receiving three-dimensional shape data of one or more adjacent teeth adjacent to a first tooth of a patient to which a prosthesis is to be fitted, and positional relationship data of the adjacent teeth in an oral cavity of the patient;

searching a database in which three-dimensional shape data of plural teeth, including natural teeth, and positional relationship data of the plural teeth in oral cavities of other patients are stored, by using the three-dimensional shape data and the positional relationship data of the adjacent teeth;

identifying from among the plural teeth at least one second tooth the three-dimensional shape data and the positional relationship data of which are similar to the three-dimensional shape data and the positional relationship data of the adjacent teeth, based on a matching degree indicated by a volume difference included in results of a positional alignment performed by associating points represented by the three-dimensional shape data and the positional relationship data of the adjacent teeth with points represented by the three-dimensional shape and the positional relationship data of the plural teeth stored in the database;

extracting from the database three-dimensional shape data in the form of CAD/CAM data of a third tooth adjacent to the identified at least one second tooth; and outputting the CAD/CAM data of the third tooth, the CAD/CAM data being used as beginning CAD/CAM data for developing the prosthesis corresponding to the first tooth.

2. The recording medium according to claim 1,
wherein the database further stores reverse three-dimensional shape data that is horizontally reversed, and
the searching searches the reverse three-dimensional shape data using the three-dimensional shape data and the positional relationship data of the adjacent teeth.

3. The recording medium according to claim 2,
wherein, in the searching, the searching is performed based on information including adjacent teeth which are adjacent to a part on which the prosthesis is to be mounted.

4. The recording medium according to claim 3,
wherein the process further comprises:
extracting from the database three-dimensional shape data in the form of CAD/CAM data of a plurality of third teeth adjacent to the identified at least one second tooth;
detecting an axial displacement amount between an axis of an abutment tooth on which the prosthesis is to be mounted and each of axes of the plurality of third teeth;
detecting a first matching degree between each tooth of the plurality of third teeth and each of the adjacent teeth and the abutment tooth based on at least one of an interference amount and a separation distance with the adjacent teeth and the abutment tooth by using information of the adjacent teeth and the abutment tooth of the part on which the prosthesis is to be mounted;
detecting a second matching degree between each tooth of the plurality of third teeth and an opposing tooth based on at least one of an interference amount and a separation distance with the opposing tooth by using information of a part opposite to the part on which the prosthesis is to be mounted;
calculating a priority level of each tooth of the plurality of third teeth based on at least one of the axial displacement amount, the first matching degree, and the second matching degree; and
the extracting is based on the priority level or an instruction from a user.

5. The recording medium according to claim 4, the process further comprising:
updating the database by associating each tooth stored therein with an identification of a user who selected the tooth and a number of times of selecting the tooth,
wherein, in the calculating, the priority level is corrected based on at least one of whether the tooth is a tooth of a same patient, a number of times of selecting the tooth by a user, and whether a user or the patient likes shape characteristics of the tooth.

6. A dental prosthesis design apparatus comprising:
a memory device configured to store a database in which three-dimensional shape data of plural teeth, including natural teeth, and positional relationship data of the plural teeth in oral cavities of other patients are stored; and
a processor configured to execute a computer-implemented process to obtain data for producing a dental prosthesis,
wherein the process includes:
receiving three-dimensional shape data of one or more adjacent teeth adjacent to a first tooth of a patient to which a prosthesis is to be fitted, and positional relationship data of the adjacent teeth in an oral cavity of the patient;
searching the database by using the three-dimensional shape data and the positional relationship of the adjacent teeth;
identifying from among the plural teeth at least one second tooth the three-dimensional shape data and the positional relationship data of which are similar to the three-dimensional shape data and the positional relationship data of the adjacent teeth, based on a matching degree indicated by a volume difference included in results of a positional alignment performed by associating points represented by the three-dimensional shape data and the positional relationship data of the adjacent teeth with points represented by the three-dimensional shape and the positional relationship data of the plural teeth stored in the database;
extracting from the database three-dimensional shape data in the form of CAD/CAM data of a third tooth adjacent to the identified at least one second tooth; and
outputting the CAD/CAM data of the third tooth, the CAD/CAM data being used as beginning CAD/CAM data for developing the prosthesis corresponding to the first tooth.

7. The dental prosthesis design apparatus according to claim 6,
wherein the database further stores reverse three-dimensional shape data that is horizontally reversed data relative to the three-dimensional shape data of the plural teeth of the other patients, and
the searching searches the reverse three-dimensional shape data using the three-dimensional shape data and the positional relationship data of the adjacent teeth.

8. The dental prosthesis design apparatus according to claim 7,
wherein, in the searching, the searching is performed based on information including adjacent teeth which are adjacent to a part on which the prosthesis is to be mounted.

9. The dental prosthesis design apparatus according to claim 8,
wherein the process further comprises:
extracting from the database three-dimensional shape data in the form of CAD/CAM data of a plurality of third teeth adjacent to the identified at least one second tooth;
detecting an axial displacement amount between an axis of an abutment tooth on which the prosthesis is to be mounted and each of axes of the plurality of third teeth;
detecting a first matching degree between each tooth of the plurality of third teeth and each of the adjacent teeth and the abutment tooth based on at least one of an interference amount and a separation distance with the adjacent teeth and the abutment tooth by using information of the adjacent teeth and the abutment tooth of the part on which the prosthesis is to be mounted;
detecting a second matching degree between each tooth of the plurality of third teeth and an opposing tooth based on at least one of an interference amount and a separation distance with the opposing tooth by using information of a part opposite to the part on which the prosthesis is to be mounted;
calculating a priority level of each tooth of the plurality of third teeth based on at least one of the axial displacement amount, the first matching degree, and the second matching degree; and
the extracting is based on the priority level or an instruction from a user.

10. The dental prosthesis design apparatus according to claim 9,
the process further comprising:
updating the database by associating each tooth stored therein with an identification of a user who selected the tooth and a number of times of selecting the tooth,
wherein, in the calculating, the priority level is corrected based on at least one of whether the tooth is a tooth of a same patient, a number of times of selecting the tooth by a user, and whether a user or the patient likes shape characteristics of the tooth.

11. A computer-implemented method to obtain data for producing a dental prosthesis, the method comprising:
receiving three-dimensional shape data of one or more adjacent teeth adjacent to a first tooth of a patient to which a prosthesis is to be fitted, and positional relationship data of the adjacent teeth in an oral cavity of the patient;
searching a database in which three-dimensional shape data of plural teeth, including natural teeth, and positional relationship data of the plural teeth in oral cavities of other patients are stored, by using the three-dimensional shape data and the positional relationship data of the adjacent teeth;
identifying from among the plural teeth at least one second tooth the three-dimensional shape data and the positional relationship data of which are similar to the three-dimensional shape data and the positional relationship data of the adjacent teeth, based on a matching degree indicated by a volume difference included in results of a positional alignment performed by associating points represented by the three-dimensional shape data and the positional relationship data of the adjacent teeth with points represented by the three-dimensional shape and the positional relationship data of the plural teeth stored in the database;
extracting from the database three-dimensional shape data in the form of CAD/CAM data of a third tooth adjacent to the identified at least one second tooth; and
outputting the CAD/CAM data of the third tooth, the CAD/CAM data being used as beginning CAD/CAM data for developing the prosthesis corresponding to the first tooth.

12. The method according to claim 11,
wherein the database further stores reverse three-dimensional shape data that is horizontally reversed data relative to the three-dimensional shape data of the plural teeth of the other patients, and
the searching searches the reverse three-dimensional shape data using the three-dimensional shape data and the positional relationship data of the adjacent teeth.

13. The method according to claim 12,
wherein, in the searching, the searching is performed based on information including adjacent teeth which are adjacent to a part on which the prosthesis is to be mounted.

14. The method according to claim 13, further comprising:
extracting from the database three-dimensional shape data in the form of CAD/CAM data of a plurality of third teeth adjacent to the identified at least one second tooth;
detecting an axial displacement amount between an axis of an abutment tooth on which the prosthesis is to be mounted and each of axes of the plurality of third teeth;
detecting a first matching degree between each tooth of the plurality of third teeth and each of the adjacent teeth and the abutment tooth based on at least one of an interference amount and a separation distance with the adjacent teeth and the abutment tooth by using information of the adjacent teeth and the abutment tooth of the part on which the prosthesis is to be mounted;
detecting a second matching degree between each tooth of the plurality of third teeth and an opposing tooth based on at least one of an interference amount and a separation distance with the opposing tooth by using information of a part opposite to the part on which the prosthesis is to be mounted;
calculating a priority level of each tooth of the plurality of third teeth based on at least one of the axial displacement amount, the first matching degree, and the second matching degree; and
the extracting is based on the priority level or an instruction from a user.

15. The method according to claim 14, further comprising:
updating the database by associating each tooth stored therein with an identification of a user who selected the tooth and a number of times of selecting the tooth,
wherein, in the calculating, the priority level is corrected based on at least one of whether the tooth is a tooth of a same patient, a number of times of selecting the tooth by a user, and whether a user or the patient likes shape characteristics of the tooth.

* * * * *